United States Patent
Tao et al.

(10) Patent No.: US 11,227,161 B1
(45) Date of Patent: Jan. 18, 2022

(54) PHYSIOLOGICAL SIGNAL PREDICTION METHOD

(71) Applicant: INSTITUTE OF AUTOMATION, CHINESE ACADEMY OF SCIENCES, Beijing (CN)

(72) Inventors: Jianhua Tao, Beijing (CN); Yu He, Beijing (CN); Bin Liu, Beijing (CN); Licai Sun, Beijing (CN)

(73) Assignee: Institute of Automation, Chinese Academy of Sciences, Beijing (CN)

( * ) Notice: Subject to any disclaimer, the term of this patent is extended or adjusted under 35 U.S.C. 154(b) by 0 days.

(21) Appl. No.: 17/471,485

(22) Filed: Sep. 10, 2021

(30) Foreign Application Priority Data

Feb. 22, 2021 (CN) .......................... 202110196564.7

(51) Int. Cl.
*G06K 9/00* (2006.01)
*G06K 9/46* (2006.01)
(Continued)

(52) U.S. Cl.
CPC ........ *G06K 9/00718* (2013.01); *A61B 5/7267* (2013.01); *A61B 5/7275* (2013.01);
(Continued)

(58) Field of Classification Search
CPC .......... G06K 9/00718; G06K 9/00281; G06K 9/00765; G06K 9/3241; G06K 9/4671;
(Continued)

(56) References Cited

U.S. PATENT DOCUMENTS 10,405,762 B2 * 9/2019 Teixeira ................ A61B 5/0295
10,783,632 B2 * 9/2020 Fan ........................ A61B 5/7275
(Continued)

FOREIGN PATENT DOCUMENTS

CN  105100701 A  11/2015
CN  105190691 B   6/2019
(Continued)

OTHER PUBLICATIONS

Niu, Xuesong, et al. "Robust remote heart rate estimation from face utilizing spatial-temporal attention." 2019 14th IEEE International Conference on Automatic Face & Gesture Recognition (FG 2019). IEEE, 2019. (Year: 2019).*

(Continued)

*Primary Examiner* — Jonathan S Lee
(74) *Attorney, Agent, or Firm* — Westbridge IP LLC

(57) ABSTRACT

A physiological signal prediction method includes: collecting a video file, the video file containing long-term videos, and contents of the video file containing data for a face of a single person and true physiological signal data; segmenting a single long-term video into multiple short-term video clips; extracting, by using each frame of image in each of the short-term video clips, features of interested regions for identifying physiological signals so as to form features of interested regions of a single frame; splicing, for each of the short-term video clips, features of interested regions of all fixed frames corresponding to the short-term video clip into features of interested regions of a multi-frame video, and converting the features of the interested regions of the multi-frame video into a spatio-temporal graph; inputting the spatio-temporal graph into a deep learning model for training, and using the trained deep learning model to predict physiological signal parameters.

8 Claims, 2 Drawing Sheets

(51) Int. Cl.
  *G06K 9/32*    (2006.01)
  *G06T 7/11*    (2017.01)
  *G06N 3/08*    (2006.01)
  *A61B 5/00*    (2006.01)
  *G06N 3/04*    (2006.01)

(52) U.S. Cl.
  CPC ..... *G06K 9/00281* (2013.01); *G06K 9/00765* (2013.01); *G06K 9/3241* (2013.01); *G06K 9/4671* (2013.01); *G06N 3/049* (2013.01); *G06N 3/08* (2013.01); *G06T 7/11* (2017.01); *G06T 2207/10016* (2013.01); *G06T 2207/20081* (2013.01); *G06T 2207/20084* (2013.01)

(58) Field of Classification Search
  CPC ............. G06T 7/11; G06T 2207/10016; G06T 2207/20081; G06T 2207/20084; G06N 3/049; G06N 3/08; A61B 5/7267; A61B 5/7275
  USPC ........................................................ 382/128
  See application file for complete search history.

(56) References Cited

U.S. PATENT DOCUMENTS

| | | | | |
|---|---|---|---|---|
| 11,017,902 B2* | 5/2021 | Sherkat | .................. | G06N 3/04 |
| 11,103,140 B2* | 8/2021 | Frank | .................... | A61B 5/165 |
| 11,127,164 B2* | 9/2021 | Marks | .................. | G06K 9/6257 |

FOREIGN PATENT DOCUMENTS

| | | |
|---|---|---|
| CN | 109846469 A | 6/2019 |
| CN | 110236514 A | 9/2019 |
| CN | 110236515 A | 9/2019 |
| CN | 110547783 A | 12/2019 |
| CN | 110619301 A | 12/2019 |
| CN | 110647815 A | 1/2020 |
| CN | 112381011 A | 2/2021 |
| EP | 3440991 A1 | 2/2019 |

OTHER PUBLICATIONS

Tulyakov, Sergey, et al. "Self-adaptive matrix completion for heart rate estimation from face videos under realistic conditions." Proceedings of the IEEE conference on computer vision and pattern recognition. 2016. (Year: 2016).*

Wang, Wenjin, Sander Stuijk, and Gerard De Haan. "Exploiting spatial redundancy of image sensor for motion robust rPPG." IEEE transactions on Biomedical Engineering 62.2 (2014): 415-425. (Year: 2014).*

Yu, Zitong, et al. "Transrppg: Remote photoplethysmography transformer for 3d mask face presentation attack detection." IEEE Signal Processing Letters (2021). (Year: 2021).*

Zhang, Panpan, et al. "Multi-hierarchical Convolutional Network for Efficient Remote Photoplethysmograph Signal and Heart Rate Estimation from Face Video Clips." arXiv preprint arXiv:2104.02260 (2021). (Year: 2021).*

First Office Action issued in counterpart Chinese Patent Application No. 202110196564.7, dated Apr. 8, 2021.

* cited by examiner

PHYSIOLOGICAL SIGNAL PREDICTION METHOD

CROSS-REFERENCE TO RELATED APPLICATIONS

The present disclosure claims priority to Chinese Patent Application CN202110196564.7 entitled "Physiological signal prediction method" filed on Feb. 22, 2021, the entire content of which is incorporated herein by reference.

FIELD OF THE INVENTION

This application relates to the field of data processing, and in particular to a physiological signal prediction method.

BACKGROUND OF THE INVENTION

The rPPG (Remote Photoplethysmography) that has emerged in recent years is a non-contact measurement method, which can be used to measure, for example, human blood volume parameters. Expansion and contraction of capillaries in a normal body will cause changes in blood volume. The amount of hemoglobin and blood oxygen content in blood vessels also varies over time. Considering that hemoglobin absorbs light into the skin, diffuse reflection waves will slightly vary with changes in the blood volume. As can be known from the above, a camera can capture minor periodic fluctuations in the values of red, green and blue waves over time, i.e., pulsatile information about physiological parameters, for measuring physiological signals.

Existing techniques for measuring physiological signals based on rPPG mainly relates to traditional signal processing methods such as independent component analysis (ICA), fast Fourier transform (FFT), wavelet transform (WT).

Patent Application Publication CN105100701A discloses a system and method for increasing accuracy of a physiological signal obtained from a video that monitors desired physiological function of a subject. In one embodiment, image frames of a video are received. Successive batches of image frames are processed. For each batch, pixels associated with an exposed body region of the subject are isolated and processed to obtain a time-series signal. If movement occurred during capture of these image frames that is below a pre-defined threshold level, parameters of a predictive model are updated using this batch's time-series signal. Otherwise, the last updated predictive model is used to generate a predicted time-series signal for this batch. The time-series signal is fused with the predicted time-series signal to obtain a fused time-series signal. The time-series signal for each batch is processed to obtain a physiological signal for the subject corresponding to the physiological function.

Patent Publication CN105190691B relates to a device and method for obtaining a vital sign of a subject despite motion of the subject, in particular for discriminating a vital sign such as a respiratory information signal from noise in a projection based vital signs registration. The proposed device includes: an interface that receives a set of image frames of a subject; an analysis unit that determines the amount of direction changes and/or the time distances between direction changes within an interested region (ROI, Region of Interest) in a subset of image frames comprising a number of image frames of said image set, a direction change indicating a change of the direction of motion appearing within said interested region; an evaluation unit that determines if said interested region within said subset of image frames comprises a vital sign information and/or noise by use of the determined amount of direction changes and/or the time distances for said subset of image frames; and a processor that determines the desired vital sign of the subject being included in said interested region within said subset of image frames if it is determined that said interested region within said subset of image frames comprises a vital sign information.

SUMMARY OF THE INVENTION

The present disclosure provides a physiological signal prediction method, including the following steps.

At step S1, a video file is collected, the video file containing long-term videos, and content of the video file containing data for a face of a single person. The face rotates with a certain amplitude at a certain speed, and the face has true physiological signal data.

At step S2, a single long-term video in the video file is segmented into multiple short-term video clips. Each of the short-term video clip has a fixed number of frames, and each of the short-term video clips corresponds to a true physiological signal tag.

At step S3, with each frame of image in each of the short-term video clips, features of interested regions for identifying physiological signals are extracted so as to form features of interested regions of a single frame.

At step S4, for each of the short-term video clips, the features of the interested regions of all fixed frames corresponding to the short-term video clip are spliced so as to form features of interested regions of a multi-frame video, and the features of the interested regions of the multi-frame video are converted from an RGB color space to a YUV color space so as to form a spatio-temporal graph containing temporal and spatial dimensions.

At step S5, the spatio-temporal graph is input into a deep learning model for training, and the trained deep learning model is used to predict physiological signal parameters.

In an exemplary embodiment of the present disclosure, if the deep learning model is a two-dimensional deep learning model, a spatio-temporal graph for each of the short-term video clips and a true physiological signal tag corresponding to each of the short-term video clips are used to train the deep learning model.

In another exemplary embodiment of the present disclosure, if the deep learning model is a three-dimensional deep learning model, it is necessary to simultaneously use multiple successive spatio-temporal graphs (short video clips) and corresponding multiple true physiological signal tags to train the deep learning model.

In an exemplary embodiment of the present disclosure, the process of segmenting the single long-term video into the multiple short-term video clips may be specifically implemented in the following manners.

The long-term video is segmented, with a time interval for the physiological signal tag as a length of a window for intercepting each of the short-term video clips, and with a time point of the respective physiological signal tag as an intermediate time point within the window.

In an exemplary embodiment of the present disclosure, the process of extracting features of interested regions for identifying physiological signals by using each frame of image in each of the short-term video clips may be specifically implemented in the following manners.

Four-point coordinates of respective rectangular boxes on both cheeks are determined by means of a 68 marks method in a dlib library, and the rectangular boxes on both cheeks are selected as the interested regions for identifying physiological signals.

In an exemplary embodiment of the present disclosure, for a frame that is unidentifiable for any feature of any interested region, replacing a value of the frame that is unidentifiable for any feature of any interested region by a value of a previous frame that is identifiable for a feature of an interested region.

In an exemplary embodiment of the present disclosure, the process of extracting features of interested regions for identifying physiological signals by using each frame of image in each of the short-term video clips may be further implemented by the following specific steps. For each frame of image in each of the short-term video clips, functions in the dlib library are used to perform face recognition, alignment, and mask face extraction.

In an exemplary embodiment of the present disclosure, the process of splicing features of interested regions of all fixed frames corresponding to the short-term video clip may be specifically implemented in the following manners.

At step S41, a feature of an interested region on one cheek of a single frame is divided uniformly into multiple rectangular zones so as to construct a matrix of pixel values.

At step S42, by taking RGB as a standard, the matrix of pixel values is reorganized to construct a reorganized matrix of pixel values.

At step S43, the reorganized matrices of pixel values on both cheeks of the face are spliced by column so as to construct a matrix of features of interested regions of a single frame.

At step S44, multiple matrices, each of them is a matrix of features of interested regions of a single frame, are spliced by column so as to form features of interested regions of a multi-frame video.

In an exemplary embodiment of the present disclosure, the process of dividing a feature of an interested region on one cheek of a single frame uniformly into the multiple rectangular zones so as to construct a matrix of pixel values may be specifically implemented in the following manners.

The feature of the interested region on one cheek of the single frame is divided uniformly into m×n rectangular zones to construct a matrix of pixel values denoted as:

$$A = \begin{bmatrix} A_{11} & \cdots & A_{1k} & \cdots & A_{1n} \\ \vdots & \ddots & & & \vdots \\ A_{i1} & & A_{ik} & & A_{in} \\ \vdots & & & \ddots & \vdots \\ A_{m1} & \cdots & A_{mk} & \cdots & A_{mn} \end{bmatrix}$$

where $A_{ik}$ represents a pixel matrix for a single rectangular zone, with a matrix dimension of [p, q, 3].

The matrix dimension of $A_{ik}$ is readjusted into [p×q, 3], where 3 columns correspond to RGB channels, respectively.

In an exemplary embodiment of the present disclosure, the process of reorganizing the matrix of pixel values by taking RGB as the standard may be implemented in the following manners.

The pixel values in the $A_{ik}$ are averaged by column for R, G, and B channels, respectively, to construct a matrix denoted as $\overline{A}_{ik} = [\overline{R}\ \overline{G}\ \overline{B}]$ with a matrix dimension of [1, 3].

$\overline{A}_1 \ldots \overline{A}_{ik} \ldots \overline{A}_{mn}$ may be spliced into a [mn, 3]-dimensional matrix by column, which matrix is denoted as:

$$B = [\overline{A}_{11} \ldots \overline{A}_{1n} \ldots \overline{A}_{i1} \ldots \overline{A}_{in} \ldots \overline{A}_{m1} \ldots \overline{A}_{mn}]^T.$$

In an exemplary embodiment of the present disclosure, the process of splicing the matrices of pixel values on both cheeks by column to construct a matrix of features of interested regions of a single frame may be specifically implemented in the following manners.

The reorganized matrices of pixel values on both cheeks are spliced into a [2mn, 3]-dimensional matrix by column, which is denoted as Bd[t], namely a matrix of features of interested regions of the t-th frame.

The process of splicing multiple matrices, each of them is a matrix of features of interested regions of a single frame, by column so as to form features of interested regions of a multi-frame video may further includes the following step.

Matrices of features of interested regions of T frames are spliced by column into a matrix denoted as:

$$C = [Bd[1] \ldots Bd[t] \ldots Bd[T]]^T.$$

The matrix C describes the features of interested regions of a multi-frame video.

In an exemplary embodiment of the present disclosure, the deep learning model is a three-dimensional convolutional neural network model or a two-dimensional convolutional neural network model with a residual network as the core. The spatio-temporal graph is input into the three-dimensional convolutional neural network model or the two-dimensional convolutional neural network model for training, and the trained three-dimensional convolutional neural network model or the trained two-dimensional convolutional neural network model is used to predict the physiological signal parameters.

Compared with the existing solutions, the above solution provided by the embodiments of the present disclosure has the following advantages.

The method provided by embodiments of the present disclosure is implemented, for a video with physiological parameter tags, to intercept video clips with a fixed number of frames, to convert them into a spatio-temporal graph, which contains pulsatile information about physiological signals, to input the spatio-temporal graph into a deep learning model for training, and to use the trained deep learning model to predict personal physiological parameters.

Meanwhile, considering that ambient noises such as substantial and rapid head rotation or changes in illumination will cause the physiological signal values to fluctuate sharply in a short period of time, the method provided in the embodiments of the disclosure selects spatio-temporal graphs corresponding to multiple video clips segmented from a same video as the input of a 3D deep learning model for learning. In this way, the model can satisfy slight changes in physiological signals during a short period—that is, the waveform of physiological signal values as a function of time fluctuates less, thereby improving the stability and robustness of physiological parameter prediction.

BRIEF DESCRIPTION OF THE DRAWINGS

The accompanying drawings, which are incorporated in and constitute a part of this specification, illustrate exemplary embodiments of the present disclosure, and together with the description serve to explain the principles of the disclosure.

In order to more clearly explain the embodiments of the present disclosure or the technical solutions in the existing technologies, drawings that need to be used in the description of the embodiments or the existing technologies will be briefly introduced below. Obviously, for those of ordinary skill in the art, other drawings can be obtained based on these drawings without any creative effort.

DETAILED DESCRIPTION OF THE EMBODIMENTS

In order to make the objectives, technical solutions and advantages of the present disclosure clearer, the technical solutions in the embodiments of the present disclosure will be further described in detail in conjunction with the accompanying figures showing exemplary embodiments of the disclosure. Obviously, the described embodiments are only part of the embodiments of the present invention, rather than all of the embodiments thereof. All other embodiments obtained based on embodiments in the present disclosure by those of ordinary skill in the art without any creative effort fall within the scope of the present disclosure.

Embodiment One

Figure 1:
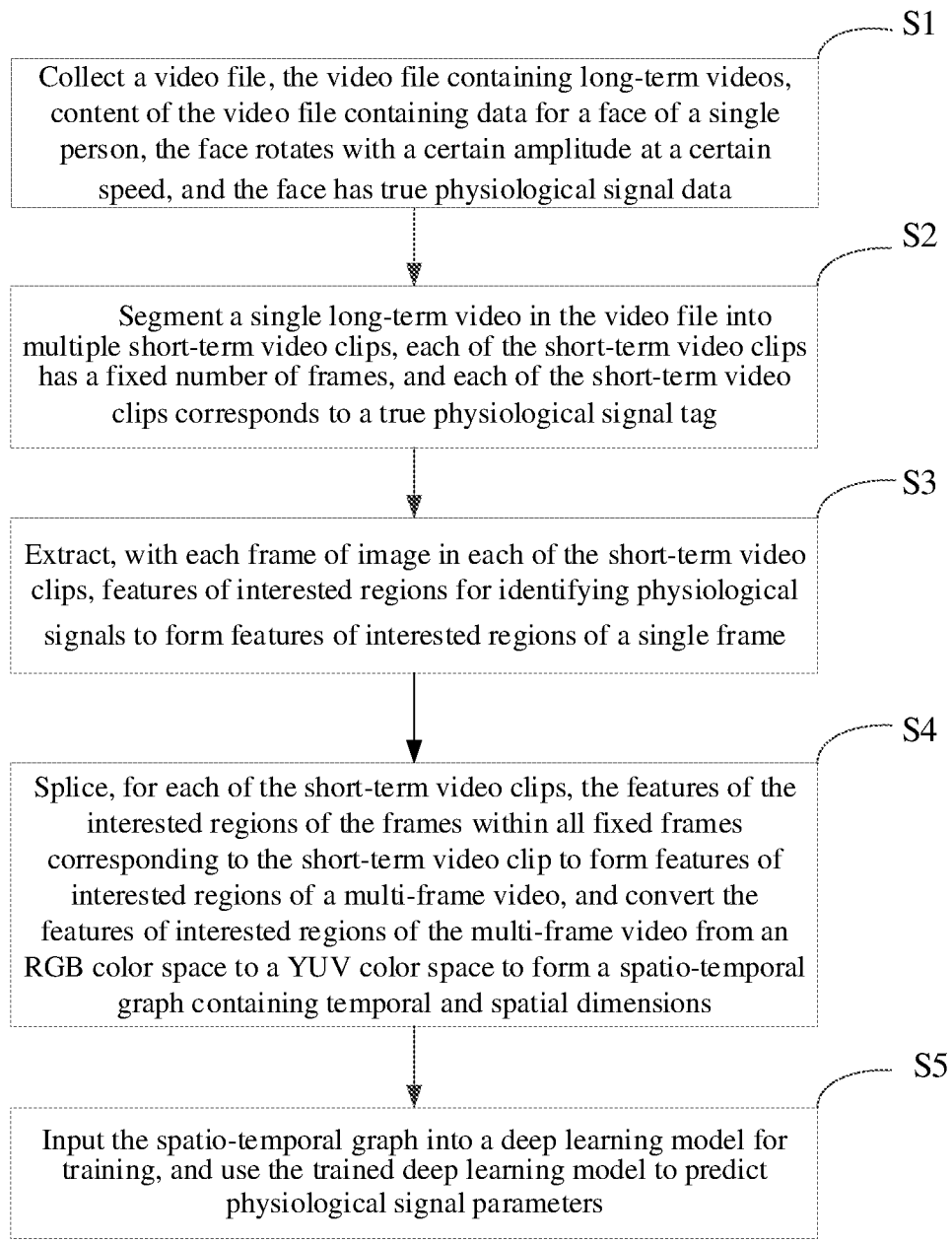
FIG. 1 is a flowchart illustrating a physiological signal prediction method provided by an embodiment of the present disclosure.

As shown in FIG. 1, a physiological signal prediction method provided by an embodiment of the present application includes the following steps.

At step S1, a video file is collected, the video file containing long-term videos, and content of the video file containing data for a face of a single person. The face may rotate with a certain velocity at a certain speed, and the face has true physiological signal data.

At step S2, a single long-term video in the video file is segmented into multiple short-term video clips. For example, the long-term video is segmented, with a time interval for the physiological signal tag as a length of a window for intercepting each of the short-term video clips, and with a time point of the respective physiological signal tag as an intermediate time point within the window. Each of the short-term video clip has a fixed number of frames, and each of the short-term video clips corresponds to a true physiological signal tag. In this embodiment, each short video file needs to be stored in an uncompressed manner, and the file format can be .avi.

At step S3: in this embodiment, for each frame of image in each of the short-term video clips, functions in the dlib library are used to perform face recognition, alignment, and mask face extraction. In this embodiment, four-point coordinates of respective rectangular boxes on both cheeks are determined by means of a 68 marks method in a dlib library, and the rectangular boxes on both cheeks are selected as the interested regions for identifying physiological signals, from which the features of the interested regions for identifying physiological signals are extracted, to form features of interested regions of a single frame.

The reasons for this is that, on the one hand, the positions of the cheeks will not be easily obstructed, and on the other hand blood flows at the positions of the cheeks will be higher. Choosing such positions as feature extraction regions can obtain a good prediction effect.

In some embodiments, for a frame that is unidentifiable for any feature of any interested region, replacing a value of the frame that is unidentifiable for any feature of any interested region by a value of a previous frame that is identifiable for a feature of an interested region, so as to ensure the continuity of the spatio-temporal graph in its temporal dimension. Usually, unidentifiable video frames will be replaced by black pixels by default. Herein, the value of the previous identifiable frame can be used to replace the value of the unidentifiable frame, which means that an approximate video frame value is inserted here. Therefore, it can avoid negative effects of large difference in pixel values on the model prediction.

At step S4, for each of the short-term video clips, the features of the interested regions of all fixed frames corresponding to the short-term video clip are spliced so as to form features of interested regions of a multi-frame video, and the features of the interested regions of the multi-frame video are converted from an RGB color space to a YUV color space so as to form a spatio-temporal graph containing temporal and spatial dimensions.

Figure 2:
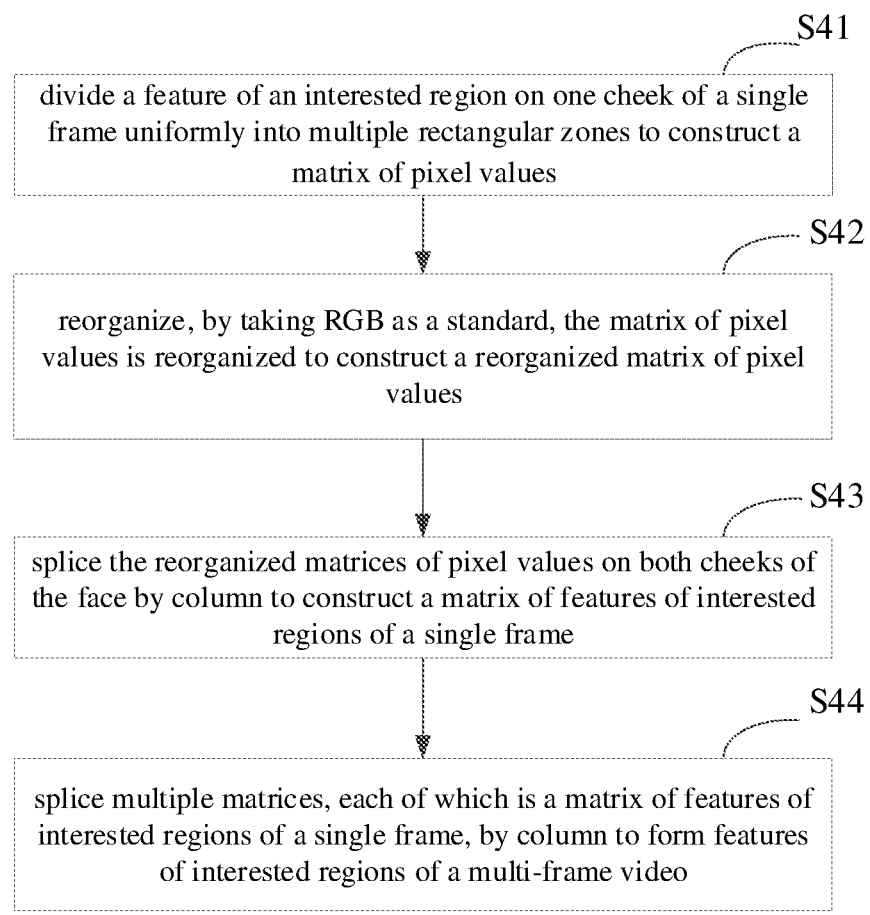
FIG. 2 is a flowchart illustrating the process of splicing features of interested regions of each frame of image in the short-term video clip according to the physiological signal prediction method provided by an embodiment of the present disclosure.

In some embodiments, as shown in FIG. 2, the process of splicing features of interested regions of each frame of image in the short-term video clip may be specifically implemented in the following manners.

At step S41, a feature of an interested region on one cheek of a single frame is divided uniformly into multiple rectangular zones so as to construct a matrix of pixel values.

In some embodiments, the process of dividing a feature of an interested region on one cheek of a single frame uniformly into the multiple rectangular zones so as to construct a matrix of pixel values may be specifically implemented in the following manners.

The feature of the interested region on one cheek of the single frame is divided uniformly into m×n rectangular zones to construct a matrix of pixel values denoted as:

$$A = \begin{bmatrix} A_{11} & \cdots & A_{1k} & \cdots & A_{1n} \\ \vdots & \ddots & & & \vdots \\ A_{i1} & & A_{ik} & & A_{in} \\ \vdots & & & \ddots & \vdots \\ A_{m1} & \cdots & A_{mk} & \cdots & A_{mn} \end{bmatrix}$$

where $A_{ik}$ represents a pixel matrix for a single rectangular zone, with a matrix dimension of [p, q, 3], where i=1 ... m, and k=1 ... n. p and q correspond to height h and width w of a custom pixel matrix A, respectively, p*m is height H of the matrix A, and q*n is width W of the matrix A.

The matrix dimension of the $A_{ik}$ is readjusted into [p×q, 3], where 3 columns correspond to RGB channels, respectively.

At step S42, by taking RGB as a standard, the matrix of pixel values is reorganized to construct a reorganized matrix of pixel values.

The pixel values in the $A_{ik}$ are averaged by column for R, G, and B channels, respectively, to construct a matrix with a matrix dimension of [1, 3] denoted as:

$$\overline{A}_{ik} = [\overline{R} \ \overline{G} \ \overline{B}].$$

$\overline{A}_1 \ldots \overline{A}_{ik} \ldots \overline{A}_{mn}$ may be spliced into a [mn, 3]-dimensional matrix by column, which matrix is denoted as:

$$B = [\overline{A}_{11} \ldots \overline{A}_{1n} \ldots \overline{A}_{i1} \ldots \overline{A}_{in} \ldots \overline{A}_{m1} \ldots \overline{A}_{mn}]^T.$$

At step S43, the reorganized matrices of pixel values of interested regions on both cheeks are spliced into a [2mn, 3]-dimensional matrix by column to construct a matrix of features of interested regions of a single frame, which is denoted as Bd[t], namely a matrix of features of interested regions of the t-th frame, where t=1 . . . T, and T is the fixed number of frames in each short-term video clip.

At step S44, multiple matrices, each of them is a matrix of features of interested regions of a single frame, are spliced by column so as to form features of interested regions of a multi-frame video.

Specifically, matrices of features of interested regions of T frames are spliced by column into a matrix denoted as:

$$C=[Bd[1] \ldots Bd[t] \ldots Bd[T]]^T.$$

The matrix C describes the features of interested regions of a multi-frame video.

At step S5, the spatio-temporal graph is input into a deep learning model for training, and the trained deep learning model is used to predict physiological signal parameters.

In fact, a short video segment corresponds to a physiological signal tag, corresponds to a spatio-temporal graph, and corresponds to multiple picture frames, each picture frame corresponds to two interested regions (left and right cheeks). Each physiological signal tag is used to characterize a set of physiological signal data, which can reflect pulsatile information about facial physiological parameters in a short video segment.

The deep learning model is a three-dimensional convolutional neural network model or a two-dimensional convolutional neural network model with a residual network as the core. The spatio-temporal graph is input into the three-dimensional convolutional neural network model or the two-dimensional convolutional neural network model for training, and the trained three-dimensional convolutional neural network model or the trained two-dimensional convolutional neural network model is used to predict the physiological signal parameters.

In some embodiments, the three-dimensional convolutional neural network model or the two-dimensional convolutional neural network model is a convolutional neural network constructed with a residual network (ResNet) as basis. A design idea of SENet is introduced in the spatial dimension, and Squeeze-and-Excitation (SE) blocks are incorporated. Due to introduction of a design idea of Depthwise Separable Convolution and ShuffleNet, the complexity of the model is reduced under a certain performance of the model. That is, group convolution is performed on the channel dimension, which is suitable for designing a block in the case of a large channel value. Convolution kernels adopt a method of dilated convolution. Due to influence of ambient noise, the extracted spatio-temporal graph may suffer from continuous information missing or information inaccuracy, and the pooling operation may also cause loss of pulsatile information about physiological signals. Therefore, a large convolution kernel, such as a 5*5 convolution kernel, can be used and also be mixed with a 3*3 convolution kernel, or a dilated convolution can be used to increase the receptive field and reduce the amount of calculation caused by using a large convolution kernel. That is, each convolution output contains a wide range of information, which improves effectiveness of information extracted by convolution. Use of a neural network with a large convolution kernel, such as Alexnet, will greatly improve the problem of missing continuous segments of feature information for a spatio-temporal graph caused by factors such as substantial and rapid head rotation or changes in illumination. The size of convolution kernel of the first layer in Alexnet model is 11, and the receptive field is large, which can facilitate extraction of pulsatile information about physiological signals in the spatio-temporal graph. Compared with a small convolution kernel, this can weaken influence of lack of spatio-temporal graph information.

Finally, mean absolute error (MAE) and root mean square error (RMSE) are used to evaluate measurement results for the physiological signals, to draw a scatter plot with tag value-predicted value.

Embodiment Two

Opencv is used to read video frame pictures. The video frame pictures are converted from an RGB space to a grayscale space for face detection. Coordinates of picture pixels are converted to a numpy array. Four-point coordinates of a rectangle on a first side, i.e., shape[12][0], shape[54][0], shape[33][1], and shape[29][1], are determined, the enclosed rectangle representing a first interested region; and four-point coordinates of a rectangle on a second side, i.e., shape[48][0], shape[4][0], shape[33] [1], and shape[29] [1], are determined, the enclosed rectangle representing a second interested region. In the above shape[a][b], a represents a serial number of one of 68-point marks, b is 0 for an abscissa x, and b is 1 for an ordinate y.

For a specific frame that is unidentifiable for any feature of an interested region caused by influence from ambient noise, a method for processing such a frame may be implemented in the following manner.

Due to the extremely short interval between frames, a value of a physiological signal under normal conditions will not fluctuate sharply. The unidentifiable frame may be replaced by a value of a previous identifiable frame to improve robustness of a spatio-temporal graph and guarantee continuity of the spatio-temporal graph in its temporal dimension. Usually, unidentifiable video frames will be replaced by black pixels by default. However, in this implementation, the value of the previous identifiable frame can be used to replace the value of the unidentifiable frame, which means that an approximate video frame value is inserted here, thereby avoiding negative effects of large difference in pixel values on the model prediction.

An interested region on one cheek of a single frame is divided uniformly into m×n rectangular zones, to construct a matrix of pixel values denoted as:

$$A = \begin{bmatrix} A_{11} & \cdots & A_{1k} & \cdots & A_{1n} \\ \vdots & \ddots & & & \vdots \\ A_{i1} & & A_{ik} & & A_{in} \\ \vdots & & & \ddots & \vdots \\ A_{m1} & \cdots & A_{mk} & \cdots & A_{mn} \end{bmatrix}$$

where $A_{ik}$ represents a pixel matrix for a single rectangular zone, with a matrix dimension of [p, q, 3].

The matrix dimension of the $A_{ik}$ is readjusted into [p×q, 3], where 3 columns correspond to RGB channels, respectively.

The pixel values in the $A_{ik}$ are averaged by column for R, G, and B channels, respectively, to construct a matrix with a matrix dimension of [1, 3] denoted as:

$$\overline{A}_{ik}=[\overline{R}\ \overline{G}\ \overline{B}]$$

$\overline{A}_1 \ldots \overline{A}_{ik} \ldots \overline{A}_{mn}$ are spliced into a [mn, 3]-dimensional matrix by column, and the matrix is denoted as:

$$B=[\overline{A}_{11} \ldots \overline{A}_{1n} \ldots \overline{A}_{i1} \ldots \overline{A}_{in} \ldots \overline{A}_{m1} \ldots \overline{A}_{mn}]^T.$$

The reorganized matrices of pixel values of interested regions on both cheeks are spliced into a [2mn, 3]-dimensional matrix by column so as to construct a matrix of features of interested regions of a single frame, which is denoted as Bd[t], namely a matrix of features of interested regions of the t-th frame, where t=1 . . . T, and T is the fixed number of frames in each short-term video clip.

Matrices of features within T frames are spliced by column into a matrix denoted as:

$$C=[Bd[1] \ldots Bd[t] \ldots Bd[T]]^T.$$

The matrix C describes the features of interested regions of a multi-frame video.

The matrix C is converted from an RGB color space to a YUV color space to generate a spatio-temporal graph.

For example, the spatio-temporal graph has a dimension of [128, 128, 3], where length and width are both 128, and the number of channels is 3;

Input dimensions of a three-dimensional convolutional neural network model may be (batch, c, L, H, W), where c=3.

Input dimensions of a two-dimensional convolutional neural network model may be (batch, c, H, W), where c=3.

batch—the number of pieces of data processed in a batch of the model;

3—RGB channels in a color space, i.e., the number of the channels;

L—a temporal dimension, that is, one video clip is input in each batch, the number of frames contained in this clip being L;

H—a height of a spatial dimension, i.e., a height of a single spatio-temporal graph;

and

W—a width of a spatial dimension, i.e., a width of a single spatio-temporal graph.

The number of prediction results output by the three-dimensional convolutional neural network model is consistent with that of true physiological signal tags, and the number of its dimensions is the same as that of spatio-temporal graphs in the input temporal dimension L. For example, the input of the model is k spatio-temporal graphs, and the output thereof is k predicted values, which corresponds to k physiological signal tags. It should be noted here that the spatio-temporal graph is continuous in time because the short video is continuous.

A single spatio-temporal graph is input into the two-dimensional convolutional neural network model, and the output predicted by the model corresponds to a true physiological signal tag of the spatio-temporal graph.

The three-dimensional convolutional neural network model is a three-dimensional convolutional neural network model built with a residual network (ResNet) as the core. A design idea of SENet is introduced in the spatial dimension, and Squeeze-and-Excitation (SE) blocks are incorporated. The sensitivity of the pulsatile information to the three YUV channels is different. Weights of the channels learned by the model through data driving determine the degree of influence of each channel information on physiological parameters. Therefore, the model should maintain the dimensions "batch" and "L" unchanged during the application of the Squeeze-and-Excitation blocks.

The following methods can also be used to build a two-dimensional convolutional neural network model, for example, by removing information about the temporal dimension L.

(1) Squeeze: the temporal dimension L is maintained unchanged, and for input feature matrices of a single spatio-temporal graph, $u_c$, global average pooling is taken for a feature matrix corresponding to each channel according to:

$$z_c = \frac{1}{H \times W} \sum_{i=1}^{H} \sum_{j=1}^{W} u_c(i, j)$$

where $z_c$ is an average value of the channel, the subscript c represents the channel, H and W represent height and width respectively, and $u_c(i, j)$ represents matrix values of the i-th and j-th pixels.

(2) Excitation: the value of the channel is recalibrate self-adaptively, which is equivalent to calculation of the weight of the channel according to:

$$s=\sigma(W_2\delta(W_1 z))$$

where $\delta$ is a ReLu activation function, $W_1$ and $W_2$ are weights of a fully connected layer, $\sigma$ is a softmax function, applied to the spatial dimensions H and W, with the temporal dimension L unchanged; s represents the weighted weight of all channels, a one-dimensional tensor, the tensor magnitude being the number of channels; and z represents the global average pooled value of all input channels, a one-dimensional tensor, the tensor magnitude being the number of channels.

(3) The feature matrix of each channel is weighted according to:

$$U_c = u_c \times s_c$$

where $u_c$ represents a feature matrix value of a single channel c for the original input, $U_c$ represents a feature matrix value of the channel c after weighting, and $s_c$ represents a weighted value corresponding to the channel c.

The three-dimensional convolutional neural network model introduces a design idea of Depthwise Separable Convolution and ShuffleNet. Under a certain performance of the model, the complexity of the model is reduced. That is, group convolution is performed on the channel dimension, which is suitable for designing a block in the case of a large channel value.

The following methods can also be used to build a two-dimensional convolutional neural network model, for example, by removing information about the temporal dimension L.

The input is split with ½ of the number of input channels (channel split), as the input of a first branch and a second branch respectively.

1. The first branch is built through the following processes sequentially:

(1) group convolution according to 1×1×1 GConv, where the channels may be selectively divided into 3, 4, 8 groups;

(2) batch normalization on ReLu activation function or H-Swish activation function (BN ReLu or BNH-Swish);

(3) depthwise separable convolution, each channel as a group with a convolution step of 2, according to 3×3×3DWConv(stride=2);

(4) batch normalization on BN;

(5) group convolution according to 1×1×1 GConv; and (6) batch normalization on BN.

2. The second branch is built through the following processes sequentially:

global average pooling according to 3×3×3 AVG Pool (stride=2).

3. After the first and second branches are connected to Concat, channel shuffle is performed, and a shuffle block is constructed through all the above processes.

Convolution kernels adopt a method of dilated convolution. Due to influence of ambient noise, the extracted spatio-temporal graph may suffer from continuous information missing or information inaccuracy, and the pooling operation may also cause loss of pulsatile information about physiological signals. Use of dilated convolution may increase the receptive field, which means that each convolution output contains a wide range of information, thereby improving effectiveness of information extracted by convolution.

Use of a neural network with a large convolution kernel, such as Alexnet, will greatly improve the problem of missing continuous segments of feature information for a spatio-temporal graph caused by factors such as substantial and rapid head rotation or changes in illumination. In some embodiments, the size of convolution kernel of the first layer in Alexnet model is 11, and the receptive field is large, which can facilitate extraction of pulsatile information about physiological signals in the spatio-temporal graph. Compared with a small convolution kernel, this can weaken influence of lack of spatio-temporal graph information.

Physiological signal prediction can be performed over multiple channels at the same time. The extracted spatio-temporal graphs are selected for inputting, and the two-dimensional convolutional neural network model or the three-dimensional convolutional neural network model is used for training respectively, and the predicted values are output.

Mean absolute error (MAE) and root mean square error (RMSE) are used to evaluate measurement results for the physiological signals, to draw a scatter plot with tag value-predicted value as abscissa-ordinate, which is defined as:

$$MAE(\hat{y}, y) = \frac{1}{m}\sum_{i=1}^{m}|\hat{y} - y|$$

$$RMSE(\hat{y}, y) = \sqrt{\frac{1}{m}\sum_{i=1}^{m}(\hat{y} - y)^2}$$

where $\hat{y}$ represents a prediction result of the model, y represents a true physiological signal tag corresponding to a video clip, and m represents a total number of physiological signal tags.

It should be noted that relational terms such as "first" and "second" herein are used solely to distinguish one from another entity or operation, without necessarily requiring or implying any such actual relationship or order between such entities or operations. The terms "comprising", "including", or any other variation thereof, are intended to cover a non-exclusive inclusion, such that a process, a method, an article, or an apparatus that includes a series of elements not only includes those elements but also may include other elements not expressly listed or inherent to such process, method, article, or apparatus. An element preceded by "including a/an . . . " does not, without more constraints, preclude the existence of additional identical elements in the process, method, article, or apparatus that includes the element.

In the above description, only specific embodiments of the present disclosure have been provided, so that those skilled in the art can understand or implement the present disclosure. Various modifications to those embodiments will be obvious to those skilled in the art, and general principles defined herein can be implemented in other embodiments without departing from the spirit or scope of the present disclosure. Therefore, the present disclosure will not be limited to the embodiments described herein, but shall accord with the widest scope consistent with the principles and novel characteristics described and claimed herein.

What is claimed is:

1. A physiological signal prediction method, comprising:
S1, collecting a video file, the video file containing long-term videos, and content of the video file containing data for a face of a single person, wherein the face rotates with a certain amplitude at a certain speed, and the face has true physiological signal data;
S2, segmenting a single long-term video in the video file into multiple short-term video clips, wherein each of the short-term video clips has a fixed number of frames, and each of the short-term video clips corresponds to a true physiological signal tag;
S3, extracting, with each frame of image in each of the short-term video clips, features of interested regions for identifying physiological signals so as to form features of interested regions of a single frame;
S4, splicing, for each of the short-term video clips, the features of the interested regions of all fixed frames corresponding to the short-term video clip so as to form features of interested regions of a multi-frame video, and converting the features of the interested regions of the multi-frame video from an RGB color space to a YUV color space so as to form a spatio-temporal graph containing temporal and spatial dimensions;
wherein the step of splicing the features of the interested regions of all fixed frames corresponding to the short-term video clip further comprises:
S41, dividing a feature of an interested region on one cheek of a single frame uniformly into multiple rectangular zones so as to construct a matrix of pixel values;
S42, reorganizing, by taking RGB as a standard, the matrix of pixel values to construct a reorganized matrix of pixel values;
S43, splicing the reorganized matrices of pixel values on both cheeks of the face by column so as to construct a matrix of features of interested regions of a single frame; and
S44, splicing multiple matrices, each of which is a matrix of features of interested regions of a single frame, by column so as to form features of interested regions of a multi-frame video; and
wherein the step of dividing a feature of an interested region on one cheek of a single frame uniformly into the multiple rectangular zones so as to construct a matrix of pixel values further comprises:
dividing the feature of the interested region on one cheek of the single frame uniformly into m×n rectangular zones to construct a matrix of pixel values denoted as:

$$A = \begin{bmatrix} A_{11} & \cdots & A_{1k} & \cdots & A_{1n} \\ \vdots & \ddots & & & \vdots \\ A_{i1} & & A_{ik} & & A_{in} \\ \vdots & & & \ddots & \vdots \\ A_{m1} & \cdots & A_{mk} & \cdots & A_{mn} \end{bmatrix}$$

where $A_{ik}$ represents a pixel matrix for a single rectangular zone, with a matrix dimension of [p, q, 3]; and readjusting the matrix dimension of $A_{ik}$ into [p×q, 3], where 3 columns correspond to RGB channels, respectively; and S5, inputting the spatio-temporal graph into a deep learning model for training, and using the trained deep learning model to predict physiological signal parameters.

2. The physiological signal prediction method according to claim 1, wherein the step of segmenting the single long-term video into the multiple short-term video clips comprises:

segmenting the long-term video, with a time interval for the physiological signal tag as a length of a window for intercepting each of the short-term video clips, and with a time point of the respective physiological signal tag as an intermediate time point within the window.

3. The physiological signal prediction method according to claim 1, wherein the step of extracting the features of the interested regions for identifying physiological signals by using each frame of image in each of the short-term video clips comprises:

determining four-point coordinates of respective rectangular boxes on both cheeks by means of a 68 marks method in a dlib library, and selecting the rectangular boxes on both cheeks as the interested regions for identifying physiological signals.

4. The physiological signal prediction method according to claim 3, wherein for a frame that is unidentifiable for any feature of any interested region, replacing a value of the frame that is unidentifiable for any feature of any interested region by a value of a previous frame that is identifiable for a feature of an interested region.

5. The physiological signal prediction method according to claim 3, wherein the step of extracting the features of the interested regions for identifying physiological signals by using each frame of image in each of the short-term video clips further comprises: using, for each frame of image in each of the short-term video clips, functions in the dlib library to perform face recognition, alignment, and mask face extraction.

6. The physiological signal prediction method according to claim 1, wherein the step of reorganizing the matrix of pixel values by taking RGB as the standard comprises:

averaging the pixel values in the $A_{ik}$ by column for R, G, and B channels, respectively, to construct a matrix denoted as $\overline{A}_{ik}=[\overline{R}\ \overline{G}\ \overline{B}]$ with a matrix dimension of [1, 3]; and splicing $\overline{A}_1 \ldots \overline{A}_{ik} \ldots \overline{A}_{mn}$ into a [mn, 3]-dimensional matrix by column, which matrix is denoted as:

$B=[\overline{A}_{11} \ldots \overline{A}_{1n} \ldots \overline{A}_{i1} \ldots \overline{A}_{in} \ldots \overline{A}_{m1} \ldots \overline{A}_{mn}]^T.$ 7. The physiological signal prediction method according to claim 6, wherein the step of splicing the reorganized matrices of pixel values on both cheeks by column to construct a matrix of features of interested regions of a single frame comprises:

splicing the reorganized matrices of pixel values on both cheeks into a [2mn, 3]-dimensional matrix by column, which is denoted as Bd[t], a matrix of features of interested regions of the t-th frame; and the steps of splicing the multiple matrices, each of which is a matrix of features of interested regions of a single frame, by column so as to form features of interested regions of a multi-frame video comprises:

splicing matrices of features of interested regions of T frames by column into a matrix denoted as:

$C=[Bd[1] \ldots Bd[t] \ldots Bd[T]]^T.$

8. The physiological signal prediction method according to claim 7, wherein the deep learning model is a three-dimensional convolutional neural network model or a two-dimensional convolutional neural network model with a residual network as the core; and inputting the spatio-temporal graph into the three-dimensional convolutional neural network model or the two-dimensional convolutional neural network model for training, and using the trained three-dimensional convolutional neural network model or the trained two-dimensional convolutional neural network model to predict the physiological signal parameters.

* * * * *